(12) United States Patent
Horinouchi et al.

(10) Patent No.: US 7,399,638 B2
(45) Date of Patent: Jul. 15, 2008

(54) PREDICTION METHOD FOR LIPIDOSIS

(75) Inventors: Akira Horinouchi, Osaka (JP); Ikuo Mori, Kawabe-gun (JP); Mika Murabayashi, Suita (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 2 days.

(21) Appl. No.: 10/584,366

(22) PCT Filed: Dec. 24, 2004

(86) PCT No.: PCT/JP2004/019758

§ 371 (c)(1),
(2), (4) Date: Jun. 23, 2006

(87) PCT Pub. No.: WO2005/064344

PCT Pub. Date: Jul. 14, 2005

(65) Prior Publication Data

US 2007/0166829 A1 Jul. 19, 2007

(30) Foreign Application Priority Data

Dec. 26, 2003 (JP) .............................. 2003-434151
Jun. 7, 2004 (JP) .............................. 2004-168849

(51) Int. Cl.
*G01N 33/92* (2006.01)
*G01N 33/48* (2006.01)

(52) U.S. Cl. .............................. 436/71; 436/63; 436/86

(58) Field of Classification Search .................. 436/63, 436/71, 86

See application file for complete search history.

(56) References Cited

U.S. PATENT DOCUMENTS 6,306,603 B1  10/2001  Oka et al.
6,828,114 B1  12/2004  Miyazaki et al.

FOREIGN PATENT DOCUMENTS

| EP | 0 361 468 B1 | 5/1993 |
|---|---|---|
| EP | 1 142 996 A1 | 10/2001 |
| JP | 2-216460 | 8/1990 |
| JP | 2000-239300 | 9/2000 |
| JP | 2001-66314 | 3/2001 |
| JP | 2001-066314 | 3/2001 |
| JP | 2001-149082 | 6/2001 |
| WO | WO00/37632 | 6/2000 |

OTHER PUBLICATIONS

Nicholls et al. Biomarkers, vol. 5, No. 6, 2000, pp. 410-423.*
Delaney et al. Biomarkers, vol. 9, No. 3, May-Jun. 2004, pp. 271-290.*
Mortuza et al., "Biochimica et Biophysica Acta", 1631(2):136-46 (2002).
Database Biosis[Onlilno] Biosciences Information Service, Philadelphia, PA, US; Jun. 1999, Vansteenhouse Jan L. et al., "Urinary orotic acid-to-creatinine ratios in cat with hepatic lipidosis" XP-002464289 (Database accession No. PREV199900289670).
J.R. Espina et al., "Detection of in vivo biomarkers of phospholipidosis using NMR-based metabonomic approaches," Magnetic Resonance in Chemistry, 39: 559-565 (2001).
H. Idborg-Bjorkman et al., "Screening of Biomarkers in Rat Urine Using LC/Electrospray Ionization-MS and Two-Way Data Analysis," Anal. Chem., 75: 4784-4792 (2003).
The 43rd Annual meeting of the Society of Toxicology, Abstracts/ Toxicology 194 (2004) 206-207.
The 43rd Annual Meeting of the Society of Toxicology, Continuing Education Course AM04 Of Mice and Magnets: Metabonomics in Safety Assessment 3.1-3.18, Mar. 21, 2004.
J. Toxicol. Sci., 29(4): 428 (2004).
D. Rudmann et al., Epididymal and Systemic Phospholipidosis in Rats and Dogs Treated with the Dopammine D3 Selective Antagonist PNU-177864, Toxicol. Pathol., 32: 326-332 (2004).
L. Zimmerman et al., "Phenylacetylglutamine and Hippuric Acid in Uremic and Healthy Subjects," Nephron 55: 265-271 (1990).

* cited by examiner

*Primary Examiner*—Maureen M Wallenhorst
(74) *Attorney, Agent, or Firm*—David G. Colin; Kathryn A. Piffat; Edwards Angell Palmer & Dodge LLP

(57) ABSTRACT

The present invention provides a prediction method for lipidosis caused by a compound, which includes detecting (a) phenylacetylglycine and/or phenylacetylglutamine, or an optionally chosen metabolic intermediate in the metabolic pathway from phenylalanine to phenylacetylglycine or phenylacetylglutamine, and (b) hippuric acid or an optionally chosen metabolic intermediate in the metabolic pathway from phenylalanine to hippuric acid, in a sample collected from a mammal receiving the compound or a mammalian cell or tissue culture exposed to the compound, and predicting the compound's potential for inducing lipidosis with the quantitative ratio of the two as the index. The present invention also provides a diagnostic method for lipidosis and diseases related thereto, including detecting (a) and (b) above in a sample collected from a mammal, and making a diagnosis with the quantitative ratio of the two as the index.

10 Claims, 1 Drawing Sheet

US 7,399,638 B2

PREDICTION METHOD FOR LIPIDOSIS

CROSS-REFERENCES TO RELATED APPLICATIONS

The present application is the 35 U.S.C. §371 national stage of PCT application PCT/JP2004/019758, filed Dec. 24, 2004, which claims benefit of Japanese application 2003-434151, filed Dec. 26, 2003, and of Japanese application 2004-168849, filed Jun. 7, 2004, the disclosures of all of which are incorporated herein by reference.

TECHNICAL FIELD

The present invention relates to a prediction method for lipidosis and a tool for the same. More specifically, the present invention relates to a prediction method for lipidosis induced by a pharmaceutical candidate compound with a balance change in the phenylalanine metabolic pathway as the index, and a diagnostic method for lipidosis due to an existing drug, or lipidosis such as hereditary lipidosis or fatty acid metabolism homeostasis abnormalities and a disease related thereto.

BACKGROUND ART

Lipidosis, characterized by the accumulation of lipids such as phospholipids, neutral fats, and sphingomyelin in living tissue with the administration of a drug, is called phospholipidosis, steatosis, sphingolipidosis and the like, respectively, according to the kind of accumulating lipid, and is also generically referred to as drug-induced lipidosis. Many of lipidosis-inducing compounds have a structure wherein both a hydrophobic region and a positively charged hydrophilic region in the molecule, i.e., what is called a cationic amphiphilic drug (CAD) structure.

In recent years, with the advance in genome analysis, orphan receptors have been recognized as valuable as drug innovation targets, and receptor agonists or antagonists have been developed, but some of such compounds have a CAD structure, which sometimes leads to the induction of lipidosis and eventually interferes with pharmaceutical development. Additionally, some of approved pharmaceuticals have been reported to cause lipidosis as an adverse drug reaction.

Currently, in a toxicity evaluation study of a pharmaceutical candidate compound, it is common practice to administer the compound to a laboratory animal such as the rat and examine histopathological changes by electron microscopy, but histopathological changes of lipidosis are often not manifested unless the compound is administered for a long time; furthermore, there are additional drawbacks, including the time and labor required for tissue specimen preparation and toxicity detection. In particular, to quickly predict the presence or absence of toxicity, and to efficiently optimize the structure, in the initial stage of drug innovation, it is essential to construct a screening system enabling the evaluation of multiple specimens more conveniently and in shorter time.

In diagnosing adverse drug reactions in toxicity studies in clinical studies and patients on medication, the applicability of the above-described method, which necessitates the collection of biopsy specimen, is largely limited because of the major surgical invasion. Therefore, there is an urgent demand for the development of an evaluation system enabling the efficient and non-invasive prediction or diagnosis of drug-induced lipidosis.

As an example of the non-invasive method of predicting and diagnosing lipidosis, a method comprising detecting the occurrence of cytoplasm-vacuolated lymphocytes in peripheral blood can be mentioned, but this is not only problematic in terms of efficiency as it necessitates microscopic examination of blood smear specimen and for other reasons, but also inadequate in terms of the reliability of prediction and diagnosis as it is known that a considerable percentage of lipidosis-inducing compounds do not cause the occurrence of vacuolated lymphocytes in peripheral blood and have only a particular organ as the target.

Metabonomics, which is to comprehensively analyze intermediate and final metabolites in peripheral humoral fluids (urine, plasma and the like), organs or cells, is coming to be utilized as an approach to monitoring changes in biological reactions, which will follow transcriptomics and proteomics, in various areas of medicine and biology. In the area of toxicology as well, this technology has begun to be utilized for research into the elucidation of toxicity development mechanisms and the prediction of toxicity; the technology, along with toxicogenomics and toxicoproteomics, is expected to find applications in drug safety evaluations and clinical diagnosis as a technology providing suggestion for molecular toxicological endpoints that will replace conventional toxicological endpoints (symptoms, laboratory testing, histopathological examination and the like) (see, for example, J. K. Nicholson et al., *Nat. Rev. Drug Discov.*, 1: 153-161, 2002 and J. C. Lindon et al., *Toxicol. Appl. Pharmacol.*, 187: 137-146, 2003).

Toxic phenomena are considered to be accompanied not only by independent changes in a single metabolite, but also by integral changes in various intermediate and final metabolites localized in a plurality of metabolic pathways. Hence, it is expected that using a technique enabling the simultaneous detection of signals from nearly all metabolites, such as nuclear magnetic resonance (NMR), will make it possible to comprehensively interpret the behavior of biological molecules involved in toxicity development.

Regarding association with drug-induced lipidosis, it has been reported that as a result of an analysis of urine from rats receiving drugs known to induce phospholipidosis (hereinafter also abbreviated as "PLsis") using proton NMR ($^1$H NMR), changes in various metabolites were observed, with phenaceturic acid (phenylacetylglycine; PAG) increased in common by drug administration (J. R. Espina et al., *Magn. Reson. Chem.*, 39: 559-565, 2001), suggesting that PAG may be used as a biomarker for the potential of drugs for inducing PLsis. However, there is no knowledge about multiple drugs, and the reliability thereof as actual markers remains unknown (for example, in *Society of Toxicology* 43rd Annual Meeting Abstracts/*Toxicology* 194 (2004) 206-207, urinary PAG is described as being effective as a biomarker not only for PLsis but also for other lipidosis, whereas in *Analytical Chemistry*, 75: 4784-4792 (2003), PAG is judged to be no more than a weak biomarker for PLsis).

DISCLOSURE OF THE INVENTION

It is an object of the present invention to provide a prediction method for lipidosis caused by a compound, useful in toxicity screening of pharmaceutical candidate compounds. It is another object of the present invention to provide a diagnostic method, particularly a non-invasive diagnostic method, for lipidosis as an adverse drug reaction caused by an existing pharmaceutical. It is still another object of the present invention to provide a diagnostic method enabling the diagnosis not only of drug-induced lipidosis, but also of a broader range of lipidosis, such as hereditary lipidosis and fatty acid metabolism homeostasis abnormalities, and diseases related thereto.

With the aim of accomplishing the above-described objects, the present inventors analyzed urine from rats receiving various pharmaceutical compounds that potentially induce or do not potentially induce lipidosis for 3 days by $^1$H NMR and examined the metabolite profiles thereof, and, as a result, the inventors found that an increase in PAG and a decrease in hippuric acid were observed in common in rats receiving a lipidosis-inducing compound. Thus, the present inventors calculated the quantitative ratio of PAG and hippuric acid in the urine from each rat, and compared the calculated results with the results of peripheral blood testing and histopathological examination; the inventors found a good correlation between this ratio and the occurrence of vacuolated lymphocytes and the lipid accumulation in the cells of various target organs, demonstrating that the mutually associated changes in PAG and hippuric acid can serve as an index of drug-induced lipidosis.

Furthermore, unexpectedly, it was found that even for lipidosis-inducing compounds that have not produced a positive change in peripheral blood testing or histopathological examination with short-time administration for 3 days, toxicity can be detected, provided that the quantitative ratio of PAG and hippuric acid is used as the index; this ratio was shown to be useful in the early diagnosis of drug-induced lipidosis.

A similar drug administration study was performed in monkeys, urinary phenylacetylglutamine (hereinafter also abbreviated as "PAGN"; in humans, monkeys and the like, phenylacetyl CoA undergoes glutamine conjugation, rather than glycine conjugation, and is excreted as PAGN in urine) and hippuric acid were measured, and the quantitative ratio thereof was calculated; a significant increase in the PAGN/hippuric acid ratio was observed in common in all monkeys receiving a lipidosis-inducing compound. Thus, it was shown that the PAG (PAGN)/hippuric acid ratio can serve as an index of drug-induced lipidosis not only in rats, but also in all mammals, including humans.

The present inventors conducted further investigations based on these findings, and developed the present invention.

Accordingly, the present invention provides the following:

[1] a prediction method for lipidosis by a compound, which comprises:
  (1) detecting (a) phenylacetylglycine and/or phenylacetylglutamine, or an optionally chosen metabolic intermediate in the metabolic pathway from phenylalanine to phenylacetylglycine or phenylacetylglutamine, and (b) hippuric acid or an optionally chosen metabolic intermediate in the metabolic pathway from phenylalanine to hippuric acid, in a sample collected from a mammal receiving the compound or a mammalian cell or tissue culture exposed to the compound, and
  (2) predicting the compound's potential for inducing lipidosis with the quantitative ratio of the two as the index,
[2] the method described in [1] above, wherein the quantitative ratio of phenylacetylglycine and/or phenylacetylglutamine and hippuric acid is used as the index,
[3] the method described in [1] above, wherein the sample is urine, serum or plasma,
[4] the method described in [1] above, wherein the cell or tissue is derived from the liver, kidney or lung, or is a lymphocyte,

[5] the method described in [1] above, wherein the lipidosis develops as one or more conditions selected from the group consisting of phospholipidosis, steatosis and sphingolipidosis,
[6] a diagnostic method for lipidosis or a disease related thereto in a mammal, which comprises:
  (1) detecting (a) phenylacetylglycine and/or phenylacetylglutamine, or an optionally chosen metabolic intermediate in the metabolic pathway from phenylalanine to phenylacetylglycine or phenylacetylglutamine, and (b) hippuric acid or an optionally chosen metabolic intermediate in the metabolic pathway from phenylalanine to hippuric acid, in a sample collected from a mammal, and
  (2) making a diagnosis with the quantitative ratio of the two as the index,
[7] the method described in [6] above, wherein the quantitative ratio of phenylacetylglycine and/or phenylacetylglutamine and hippuric acid is used the index,
[8] the method described in [6] above, wherein the sample is urine, serum or plasma,
[9] the method described in [6] above, wherein the lipidosis is hereditary lipidosis, drug-induced lipidosis or fatty acid metabolism homeostasis abnormalities,
[10] the method described in [6] above, wherein the disease is selected from the group consisting of hyperlipemia, atherosclerosis, arteriosclerosis, myocardial infarction, fatty liver, hepatitis, liver cirrhosis, diabetes mellitus, dementia, Alzheimer's disease, heart disease and chronic fatigue syndrome, and the like.

Because the prediction and diagnostic methods of the present invention are not influenced by the amount of L-phenylalanine (hereinafter also abbreviated as "Phe"; the term "phenylalanine" as used herein means L-phenylalanine unless otherwise stated) taken, lipidosis can be predicated at high accuracy and high sensitivity even if the test animal is in an aggravated physiological condition due to administration of a high dose of a drug. According to the prediction and diagnostic methods of the present invention, positivity can be determined with short-time administration even for a compound with which no histopathological changes of lipidosis are manifested unless the compound is administered for a long time. Furthermore, provided that a peripheral humoral fluid such as urine or plasma is used as the sample, non-invasive diagnosis would be possible in the clinical diagnosis of lipidosis and diseases related thereto.

BEST MODE FOR EMBODYING THE INVENTION

Figure 1:
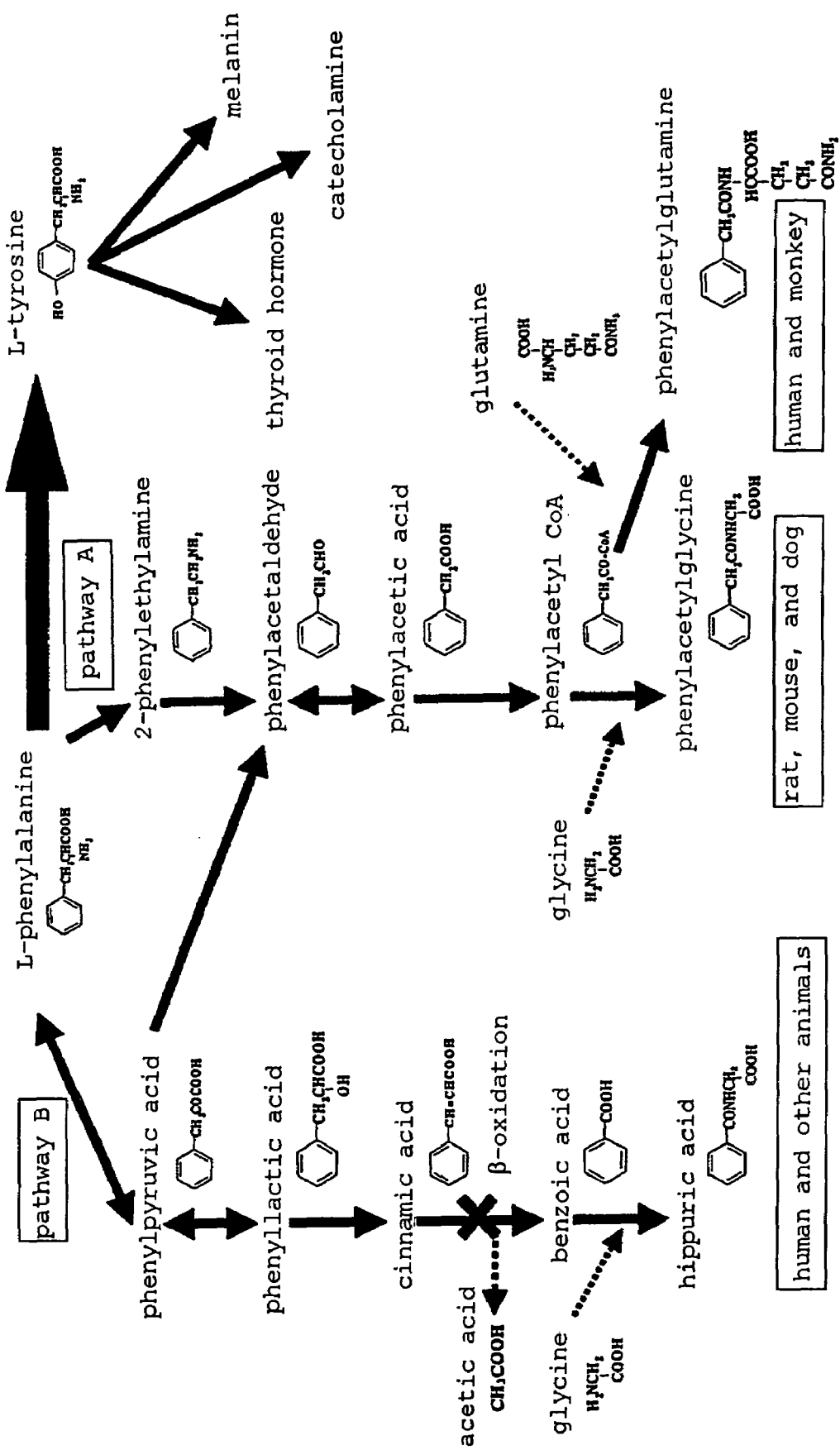
FIG. 1 shows the metabolic pathways for L-phenylalanine in mammals.

The present invention relates to a method of predicting a compound's potential for inducing lipidosis, which comprises detecting (a) PAG and/or PAGN, or an optionally chosen metabolic intermediate in the metabolic pathway from Phe to PAG or PAGN (hereinafter also generically referred to as "analyte (a)"), and (b) hippuric acid or an optionally chosen metabolic intermediate in the metabolic pathway from Phe to hippuric acid (hereinafter also generically referred to as "analyte (b)"), in a sample collected from a mammal receiving the compound or a mammalian cell or tissue culture exposed to the compound, with the quantitative ratio of the two as the index.

The mammal to which the prediction method of the present invention is applied is not subject to limitation as to animal species, as long as it has received the compound in advance; for example, humans, monkeys, rats, mice, hamsters, guinea pigs, dogs, cats, rabbits, pigs, sheep, goat, horses, cattle and the like can be mentioned. Preference is given to humans, monkeys, rats, mice and the like. The animal's sex, age, body weight and the like are not subject to limitation; varying depending on animal species, in the case of, for example, humans, healthy male adults are usually preferably chosen in phase I studies (except for therapeutics for diseases characteristic of females or children, anticancer agents and the like) from the viewpoint of maternal protection and the like. In the case of rats, individuals at about 2 months to about 24 months of age weighing about 100 g to about 700 g are preferably used, but these are not to be construed as limiting the scope of the present invention.

When the mammal is a non-human animal, it is preferable to use a genetically and microbiologically controlled population of animals. For example, it is genetically preferable to use an animal of inbred strain or closed colony; in the case of rats, inbred rats such as Sprague-Dawley (SD), Wistar, and LEW can be mentioned as examples; in the case of mice, inbred mice such as BALB/c, C57BL/6, C3H/He, DBA/2, SJL, and CBA and closed colony mice such as DDY and ICR can be mentioned, but these are not to be construed as limiting the scope of the present invention. Although the animal may be a microbiologically conventional animal, it is more preferable to use an animal of SPF (specific pathogen free) or gnotobiotic grade from the viewpoint of elimination of the influence of infectious disease.

Meantime, the mammalian cells or tissue is not subject to limitation, as long as they are cells or tissue collected from the above-described mammal, and comprising all or portion of the metabolic pathway from Phe to PAG or PAGN and all or portion of the metabolic pathway from Phe to hippuric acid; as examples, all cells [for example, hepatocytes, splenocytes, nerve cells, glial cells, β cells of pancreas, bone marrow cells, mesangial cells, Langerhans' cells, epidermic cells, epithelial cells, goblet cells, endothelial cells, smooth muscle cells, fibroblasts, fibrocytes, myocytes, adipocytes, immune cells (e.g., macrophages, T cells, B cells, natural killer cells, mast cells, neutrophils, basophils, eosinophils, monocytes), megakaryocytes, synovial cells, chondrocytes, bone cells, osteoblasts, osteoclasts, mammary gland cells, interstitial cells, or corresponding progenitor cells, stem cells, cancer cells, and the like], or from any tissues where these cells are present [for example, brain, brain regions (e.g., olfactory bulb, amygdaloid nucleus, basal ganglia, hippocampus, thalamus, hypothalamus, cerebral cortex, medulla oblongata, cerebellum), spinal cord, pituitary glands, stomach, pancreas, kidney, liver, gonad, thyroid, gall-bladder, bone marrow, adrenal gland, skin, lung, gastrointestinal tract (e.g., large intestine, small intestine), blood vessels, heart, thymus, spleen, submandibular gland, peripheral blood, prostate, testis, ovary, placenta, uterus, bone, joints, adipose tissue, skeletal muscles and the like], or cell lines established from the above-described cells and tissues and the like can be mentioned. Preferably, cells or tissue derived from liver, kidney, lung, mesenteric lymph nodes, spleen and the like, or peripheral blood lymphocytes, monocytes and the like can be mentioned. Because of the good reproducibility (particularly in the case of human cells), the ease of obtainment and the like, it is preferable to use a cell line. As examples of the human cell line, the HepG2 cell line, which is derived from liver cancer, the HEK293 cell line, which is derived from the kidney, the A549 cell line, which is derived from lung cancer, the U-937 cell line, which is derived from lymphoma, the THP-1 cell line, which is derived from monocytes, the Caco-2 cell line, which is derived from colorectal cancer, the HeLa cell line, which is derived from cervical cancer, and the like can be mentioned, but these are not to be construed as limiting the scope of the present invention.

As examples of the compound which is administered to the mammal or to which the mammalian cell or tissue is exposed, pharmaceutical or animal drug candidate compounds (compounds in the clinical study phase when the test animal is a human) and the like can be mentioned.

The method of administering the compound to the mammal is not subject to limitation; for example, the test compound can be administered orally or parenterally (e.g., intravenous, intramuscular, intraperitoneal, intra-arterial, subcutaneous, intradermal, intratracheal and the like) in the form of solid, semi-solid, liquid, aerosol and the like. The dose of the test compound varies depending on the kind of compound, animal species, body weight, dosage form, duration of administration and the like; for example, in the case of short-time administration for about 3 days, a dose required to expose the animal to the test compound at the highest concentration allowing the cells of the target organ to survive for a given time or longer, as long as the animal can survive, and the like can be mentioned. In clinical studies, various doses are chosen within the range established on the basis of the data obtained in pre-clinical studies. Administration can be performed at one time or in several divided doses. Time from administration to sample collection varies depending on the animal species, dose of the test compound, drug disposition and the like; in the case of, for example, rats, when a high dose is administered for a short time, about 1 day to about 7 days, preferably about 3 days to about 5 days, from initial administration can be mentioned. When a low dose is administered for a long time, about 1 month or more, preferably about 2 months to about 6 months, from initial administration can be mentioned.

The animal husbandry concerning feeding, watering, bright/dark phase cycling and the like during the administration period, is not subject to limitation; in the case of rats, mice and the like, for example, a method comprising rearing the animals having free access to a commercially available solid or powder food and fresh tap water or well water in a 12-hour light/dark cycle can be mentioned. The animals may be fasted and/or water-denied for a given period as necessary. Although the prediction method of the present invention is advantageous in that it is not influenced by individual differences in the amount of Phe taken, as described below, it is more preferable to use a food permitting a calculation of the amount of Phe taken from food consumption.

The sample collected from a mammal used in the prediction method of the present invention is not subject to limitation, as long as it is a biological sample in which any metabolite in the metabolic pathway from Phe to PAG or PAGN and any metabolite in the metabolic pathway from Phe to hippuric acid can be detected; for example, a peripheral humoral fluid such as urine, plasma, or serum, peripheral blood cells such as lymphocytes and monocytes, or a biopsy sample of cells or tissue derived from the liver, kidney, lung, mesenteric lymph nodes, spleen and the like, and the like can be mentioned; peripheral humoral fluids and peripheral blood cells are preferable because of the low invasion to the test animal, and peripheral humoral fluids are more preferable because of the obviation of the need for the preparation of cell extract.

As the method of collecting a peripheral humoral fluid, in the case of, for example, urine, for a human, an ordinary method of urine sampling can be mentioned; for a non-human mammal, the collection can be performed by forcedly collecting fresh urine by sacral vertebral stimulation or urinary bladder compression after a given time has elapsed following administration of the compound, or pooling spontaneously excreted urine in a urine collecting vessel using a metabolic cage for a given time (for example, about 1 hours to about 24 hours, preferably about 3 hours to about 12 hours). The latter is preferred because of the obviation of the need for a special technique, small data variation and the like. In the case of urine pooling, it is preferable to previously ice-cool the urine collection vessel to prevent changes in urinary metabolites, and toluene, thymol, concentrate hydrochloric acid and the like may be added drop by drop in small amounts as antiseptics. Furthermore, to prevent urine evaporation, a small amount of liquid paraffin may be added to the urine collection vessel. The urine collected is subjected to assay after the supernatant is purified by centrifugation and the like as necessary, and, if there is a long time lag to the assay, the urine collected may be stored under freezing and thawed before use.

Plasma can be prepared by drawing venous blood from the inside of the elbow, back of the hand and the like by an ordinary method of blood drawing for a human, or collecting blood running out from an artificially injured caudal vein, caudal artery, or orbital venous plexus using a capillary tube and the like for a non-human mammal, adding an anticoagulant such as heparin, EDTA, or sodium citrate as necessary, and separating and removing blood cells by centrifugation or filtration through a plasma separation membrane. Serum can be prepared by allowing similarly collected blood to stand for a given time or longer to form blood clots, then collecting the supernatant by centrifugation and the like. Both plasma and serum can be stored under freezing and thawed before use if there is a long time lag to the assay.

Meantime, when the sample is cells or tissue, cell or tissue extract may be prepared by treating cells or tissue derived from various organs, obtained by biopsy, or further fractionating by a conventional method a blood cell fraction after plasma separation from blood collected as described above, and treating the thus-obtained various blood cells in accordance with the method described below with regard to mammalian cell or tissue culture. This extract can also be stored under freezing and thawed before use.

The method of exposing mammalian cells or tissue to the compound is not subject to limitation; specifically, for example, when a cell line is used as the sample, cells in the cell growth phase cultured in an appropriate medium under suitable conditions are detached using trypsin-EDTA and the like and centrifuged, and the cells are recovered, after which an appropriate medium [e.g., MEM containing about 5% to about 20% fetal bovine serum (FBS) (*Science*, 122: 501 (1952)), DMEM (*Virology*, 8: 396 (1959)), RPMI 1640 medium (*The Journal of the American Medical Association*, 199: 519 (1967)), 199 medium (*Proceeding of the Society for the Biological Medicine*, 73: 1 (1950)) and the like (antibiotics such as penicillin, streptomycin and hygromycin may further be added as necessary)] is added to suspend the cells to obtain a desired cell density. Although cell density is not subject to limitation, it is preferable to adjust the cell density so that the cells retain the state in the cell growth phase. Therefore, preferable initial cell density varies depending on the growth rate of the cells used and the like, and can easily be set according to the cells used by those skilled in the art, and is normally about $5 \times 10^4$ cells/mL to about $1 \times 10^7$ cells/mL. The test compound dissolved in an appropriate solvent (or dispersed in dispersant) is further diluted with the medium, and this dilution is added to the above-described cell suspension to obtain a final concentration equal to, for example, the highest concentration allowing the cells to survive (this concentration can be determined by separately performing histopathological observation), and the cells are cultured under ordinary conditions, for example, in a $CO_2$ incubator, in an atmosphere such as 5% $CO_2$/95% air or 5% $CO_2$/5% $O_2$/90% air, at about 30° C. to about 40° C. for about 3 hours to 168 hours, preferably about 6 hours to about 72 hours, and more preferably about 12 hours to about 48 hours. As the mammalian cells or tissue, cells or tissue collected from the living body can also be used as is.

For a mammalian cell or tissue culture exposed to a compound (in the present invention, cases wherein cells or tissue collected from a living body are exposed to a compound as is, are also encompassed in the scope of culture as referred to herein because exposure to a compound unavoidably involves a step for incubating cells or tissue for a given time), either the cells/tissue or the culture supernatant, depending on the kinds of analytes (a) and (b) and the like, is collected by centrifugation, filtration and the like as appropriate, and the culture supernatant can be assayed as is, or after undergoing a treatment such as concentration as necessary, and the cells/tissue can be assayed after being prepared as a soluble fraction according to an ordinary method of extraction. For example, the mammalian cell or tissue culture can be obtained by disrupting the cells/tissue in a buffer solution for extraction such as ice-cooled phosphate buffer solution, Tris-HCl buffer solution, acetate buffer solution, or borate buffer solution, using sonication, a surfactant and the like as required, centrifuging the solution, and recovering the supernatant.

In the prediction method of the present invention, PAG and/or PAGN (hereinafter also abbreviated as "PAG/PAGN") or an optionally chosen metabolic intermediate in the metabolic pathway from Phe to PAG or PAGN (analyte (a)) and hippuric acid or an optionally chosen metabolic intermediate in the metabolic pathway from Phe to hippuric acid (analyte (b)) are detected in a specimen obtained as described above. An optionally chosen metabolic intermediate in the metabolic pathway from Phe to PAG or PAGN specifically means any of 2-phenylethylamine, phenylacetaldehyde, phenylacetic acid and phenylacetyl CoA (including conjugates thereof (excluding PAG and PAGN)); an optionally chosen metabolic intermediate in the metabolic pathway from Phe to hippuric acid means any of phenylpyruvic acid, phenyllactic acid, cinnamic acid and benzoic acid (including conjugates thereof (excluding hippuric acid)).

It is known that in mammals, Phe is mainly oxidized to L-tyrosine (Tyr) by phenylalanine hydroxylase and further converted to catecholamine, melanin and the like, with a portion of Phe being eventually metabolized to hippuric acid via phenylpyruvic acid, phenyllactic acid, cinnamic acid, and benzoic acid (pathway B in FIG. 1), or eventually metabolized to PAG (in the case of rats, mice, dogs and the like) and/or PAGN (in the case of humans, monkeys and the like) via 2-phenylethylamine, phenylacetaldehyde, phenylacetic acid, and phenylacetyl CoA (pathway A in FIG. 1), and excreted in urine. For example, in the case of humans and rats, in the normal state, much of the Phe not available in Tyr synthesis is metabolized and excreted (cleared) via pathway B, and therefore the urinary PAG(PAGN)/hippuric acid ratio is biased on the hippuric acid side. The present inventors found that the changes commonly found in the urine of rats receiving a lipidosis-inducing compound, i.e., increases in PAG and decreases in hippuric acid, are attributed to a shift of the Phe clearance balance toward greater utilization of the second pathway (pathway A), which is usually a minor pathway, for some reason.

Therefore, provided that the quantitative ratio of analyte (a) and analyte (b) in the sample is found to have increased compared to the ratio obtained without administration of the compound, the compound can be predicted to potentially induce lipidosis. Although it has been suggested that a PLsis potential for test compound can be predicted with an increase in PAG as the index, as described above, there has been neither idea to date that an increase in PAG/PAGN is viewed as a change associated with a decrease in hippuric acid, nor idea that such association is viewed as a change in the balance of the Phe clearance pathways. Since Phe is an essential amino acid for mammals and needs to be taken via food, the amount of Phe taken decreases and the amount of Phe excreted without being utilized for Tyr synthesis also decreases as food consumption decreases due, for example, to deteriorated health other than lipidosis, feeding restriction and the like. Therefore, when an increase in PAG/PAGN alone is used as the index, apparently no change in PAG/PAGN content is observed in some cases because of a decrease in the amount of Phe entering the pathway A despite an increase in the above-described the (a)/(b) ratio, resulting in the problem of a reduction in the accuracy of prediction. For this reason, to obtain the accurate predictive result, the amount of Phe taken must be precisely monitored and measured values must be corrected. In contrast, provided that the (a)/(b) ratio is used as the index, positivity/negativity can be determined only based on changes in measured value, irrespective of the amount of Phe taken (see Example 4 below), and this is outstandingly excellent in terms of convenience.

The term "quantitative ratio of analyte (a) and analyte (b)" as used herein encompasses not only the above-described (a)/(b) ratio, but also the ratio of (a) or (b) to (a)+(b). Because (a)+(b) corresponds to the amount of Phe taken, the above ratio indicates how much the ratio of Phe entering the pathway A (or B) to the entire amount of Phe entering the clearance pathways has changed. When the amount of Phe taken can be calculated, it is also possible to measure only either analyte (a) or (b), and make a comparison in terms of the ratio of the measured value to the amount of Phe taken. As the method of calculating the amount of Phe taken, feeding the test animal a food that uniformly comprises a Phe-containing ingredient and monitoring the food consumption by the animal and the like can be mentioned.

Although the combination of analyte (a) and analyte (b) is not subject to limitation, both need to be contained in the specimen. For example, when the sample collected from the mammal receiving the compound is urine, serum or plasma, analyte (a) is preferably PAG/PAGN, and analyte (b) is preferably hippuric acid, but these are not to be construed as limiting the scope of the present invention.

Analytes (a) and (b) may be detected by any assay method; both may be detected simultaneously, or may be detected separately. As examples of the method of simultaneously detecting both, methods based on nuclear magnetic resonance (e.g., $^1$H NMR, $^{13}$C NMR), gas chromatography (GC), gas chromatography-mass spectrometry (GC-MS), high performance liquid chromatography (HPLC), HPLC-NMR, liquid chromatography-mass spectrometry (LC-MS), LC-MS-MS, thin-layer chromatography-mass spectrometry (TLC-MS), capillary zone electrophoresis-mass spectrometry (CZE-MS), and immunoassay and the like can be mentioned, but these are not to be construed as limiting the scope of the present invention. Assay conditions such as various parameters in each method of detection can be easily chosen as appropriate according to the kind of analyte and the like by those skilled in the art.

For example, when PAG and hippuric acid are detected by $^1$H NMR, the detection can be achieved by, for example, the methods described in J. R. Espina et al. (2001; supra) and *Drug Metabolism and Disposition*, 26(11): 1134-1143 (1998) or methods based thereon. Specifically, the method described in an Example below and the like can be mentioned. When PAG and hippuric acid are detected by $^{13}$C NMR, the detection can be achieved by, for example, the method described in *Drug Metabolism and Disposition* (1998; supra) or a method based thereon; when phenylacetic acid is detected, the detection can be achieved by, for example, the method described in *Am. J. Physiol.*, 275(5 Pt 1): E843-E852 (1998) or a method based thereon.

When PAG and hippuric acid are detected by HPLC, the detection can be achieved by, for example, the method described in *Drug Metabolism and Disposition* (1998; supra) or a method based thereon; when hippuric acid or benzoic acid is detected, the detection can be achieved by, for example, the methods described in *Drug Metabolism and Disposition*, 31(8): 987-992 (2003) and *J. Pharmacol. Exp. Ther.*, 305(1): 279-289 (2003) or methods based thereon.

When hippuric acid and the like are detected by HPLC-NMR, the detection can be achieved by, for example, the method described in *Anal. Biochem.*, 291: 245-252 (2001) or a method based thereon.

When PAG and hippuric acid are detected by GC or GC-MS, the detection can be achieved by, for example, the methods described in *Drug Metabolism and Disposition* (1998; supra) and *Drug Metabolism and Disposition* (2003; supra) or methods based thereon.

When hippuric acid is detected by LC-MS-MS, the detection can be achieved by, for example, the methods described in *Rapid. Commun. Mass. Spectrom.*, 18: 265-272 (2004) or methods based thereon.

When PAGN is detected using immunoassay, the detection can be achieved by, for example, the methods described in the description for U.S. Pat. No. 5,100,807 or methods based thereon. In this case, when each of PAG/PAGN and hippuric acid is detected using an antibody, it is necessary to previously verify that the antibody does not cross-react with the other compound in accordance with, for example, the method described in Japanese Patent Unexamined Publication No. HEI-11-343300.

The quantitative ratio of analyte (a) and analyte (b) is measured and compared by any method described above between (1) a sample collected from a mammal receiving the compound or a mammalian cell or tissue culture exposed to the compound, and (2) a sample collected from a mammal not receiving the compound or a mammalian cell or tissue culture not exposed to the compound; if the (a)/(b) ratio [or (a)/(a)+ (b) ratio] has increased or the (b)/(a)+(b) ratio has decreased, the compound is predicted to induce lipidosis. Here, the change rate of the quantitative ratio is not subject to limitation; varying depending on animal species, type of cell, dose, duration of administration, dosage form, kind of sample and the like, for example, when urine from a rat receiving the compound for 3 days is used as the sample, provided that the (a) (=PAG)/(b) (=hippuric acid) ratio is not less than about 0.3, and when urine from a monkey receiving the compound for 7 days is used as the sample, provided that the (a) (=PAGN)/(b)(=hippuric acid) ratio is not less than about 4.0, the compound can be predicted to potentially induce lipidosis.

The lipidosis that can be predicted by the prediction method of the present invention is not subject to limitation, for example, PLsis, steatosis and sphingolipidosis and the like can be mentioned.

The accuracy of the prediction method of the present invention can be evaluated by examining biopsy samples of various target organs collected from a mammal receiving the compound for a given time (for example, about 3 days to about several months) for histopathological changes and the like, and is preferably evaluated using an animal receiving the compound at an as low dose as is used in actual practice for a long time. In high-dose administration for a short time, compounds reported to induce PLsis may sometimes test negative both for histopathological changes and vacuolated lymphocyte testing, as shown in an Example below.

Meantime, according to the prediction method of the present invention, a remarkable increase in the (a)/(b) ratio is also observed with high-dose administration for a short time, and the compound can be predicted to potentially induce lipidosis. Hence, the prediction method of the present invention enables the highly accurate determination of positivity and negativity in a shorter time, thus making it possible to streamline toxicity screening in the initial phase of pharmaceutical development, and, on the other hand, to predict the risk of developing lipidosis and reduce the risk on the subjects before specific symptoms manifested and in the clinical study phase.

The present invention is based on the finding that lipidosis can be predicted as the utilization balance for the two metabolic pathways in Phe clearance, as described above. Therefore, the method of the present invention can be used to diagnose not only lipidosis caused by drugs (i.e., drug-induced lipidosis), but also a broader range of lipidosis, and even diseases related thereto (i.e., diseases caused by lipidosis, diseases resulting in lipidosis, and the like). Accordingly, the present invention also provides a diagnostic method for lipidosis or a disease related thereto in mammals, which comprises detecting (a) PAG/PAGN or an optionally chosen metabolic intermediate in the metabolic pathway from Phe to PAG or PAGN, and (b) hippuric acid or an optionally chosen metabolic intermediate in the metabolic pathway from Phe to hippuric acid, in a sample collected from a mammal receiving the compound or a mammalian cell or tissue culture exposed to the compound, with the quantitative ratio of the two as the index. Here, all of the mammal, the sample collected from the mammal, the optionally chosen metabolic intermediate, and the quantitative ratio are the same as those described with regard to the above-described prediction method of the present invention. The term "diagnosis" as used herein refers to a concept encompassing all diagnoses, including not only the judgement on the presence or absence of suffering, but also the determinations of severity (degree of progression), likelihood of suffering/development of disease in the future, and the like after an established diagnosis is made.

As examples of lipidosis that can be diagnosed by the diagnostic method of the present invention, hereditary lipidosis (e.g., Gaucher disease, Niemann-Pick disease (types A to C), Fabry disease, Wolman disease, cholesterol ester lipidosis, cerebrotendinous xanthomatosis, phytosterolemia, Refsum syndrome, Tay-Sachs disease, generalized (GM1) gangliosidosis, sulfatide lipidosis (metachromatic leukodystrophy), galactosylceramide lipidosis and the like), drug-induced lipidosis (e.g., PLsis, steatosis, sphingolipidosis and the like), fatty acid metabolism homeostasis abnormalities (e.g., fatty acid β oxidation abnormalities and the like) and the like can be mentioned. The term "drug" as used herein encompasses drugs approved and used as pharmaceuticals or animal drugs, as well as optionally chosen drugs erroneously taken, or environmentally absorbed, by the test animal, and the like.

Regarding diseases related to lipidosis, hyperlipemia, atherosclerosis, arteriosclerosis, myocardial infarction, fatty liver, hepatitis, liver cirrhosis, diabetes mellitus, dementia, Alzheimer's disease, heart disease and chronic fatigue syndrome and the like can be mentioned as examples of diseases related to fatty acid metabolism homeostasis abnormalities, and pulmonary fibrosis, blindness, encephalopathy and the like can be mentioned as examples of diseases (adverse drug reaction symptoms) related to drug-induced lipidosis, but these are not to be construed as limiting the scope of the present invention. As examples of the disease in a non-human mammal, hepatic lipidosis and the like in companion animals such as cats and dogs can also be mentioned.

As shown in FIG. 1, in the metabolic pathway from Phe to hippuric acid, conversion of cinnamic acid to benzoic acid occurs by β oxidation. Since it has been reported in a number of documents that fatty acid β oxidation is suppressed in lipidosis, including PLsis, the changes in the utilization balance for the Phe clearance pathways in lipidosis are possibly due to the greater utilization of the metabolic pathway to PAG/PAGN because of the suppression of the conversion of cinnamic acid to benzoic acid. Therefore, the diagnostic method of the present invention may be useful in the diagnosis of, in particular, diseases associated with fatty acid β oxidation abnormalities.

The numerical value of the (a)/(b) ratio, which serves as a diagnostic criterion for the suffering (or high likelihood of suffering) of lipidosis or a disease related thereto and the like vary depending on animal species, age, sex, kind of sample collected and the like. For example, a criterion for diagnosing lipidosis with a measured value of not less than "mean+2SD" for normal animals under the same conditions and the like can be established, but these are not to be construed as limiting.

The present invention also provides a kit that can suitably used for the prediction method and diagnostic method of the present invention. The kit of the present invention comprises (a) a reagent for measurement of PAG/PAGN or an optionally chosen metabolic intermediate in the metabolic pathway from Phe to PAG or PAGN, and (b) a reagent for measurement of hippuric acid or an optionally chosen metabolic intermediate in the metabolic pathway from Phe to hippuric acid. The reagents for measurements are not subject to limitation, as long as they enable quantitative analysis, and are preferably ones comprising an antibody. When the reagents for measurement comprise antibodies, the antibody against analyte (a) and the antibody against analyte (b) used are ones that exhibit low cross-reactivity to each other to the extent that does not interfere with the measurement of the (a)/(b) ratio. The antibodies may also be any of polyclonal antibodies and monoclonal antibodies, and may be labeled or may not be labeled with a labeling agent. When the antibody against analyte (a) and/or the antibody against analyte (b) is not labeled with a labeling agent, the kit of the present invention may further comprise a labeling agent. As examples of the labeling agent, a radioisotope, enzyme, fluorescent substance, luminescent substance and the like are used. As examples of the radioisotope, $[^{125}I]$, $[^{131}I]$, $[^{3}H]$, $[^{14}C]$ and the like are used. As the above-described enzyme, stable one of high specific activity is preferable; for example, β-galactosidase, β-glucosidase, alkaline phosphatase, peroxidase, malate dehydrogenase and the like are used. As examples of the fluorescent substance, fluorescamine, fluorescein isothiocyanate and the like are used. As examples of the luminescent substance, luminol, luminol derivative, luciferin, lucigenin and the like are used. Furthermore, a biotin-(strepto)avidin system can also be used to link an antibody and a labeling agent.

An antibody contained in the kit of the present invention can be prepared by, for example, the method described in the description for U.S. Pat. No. 5,100,807 or a method based thereon. In this case, it is necessary to previously verify that the antibodies exhibit low cross-reactivity to each other to the extent that does not interfere with the measurement of the (a)/(b) ratio in accordance with, for example, the method described in Japanese Patent Unexamined Publication No. HEI-11-343300 and the like.

The kit of the present invention can also further comprise an analyte (a) and/or an analyte (b). In this case, the analyte (a) and the analyte (b) may be labeled or may not be labeled with a labeling agent. When the analyte (a) and/or the analyte (b) is not labeled with a labeling agent, the kit of the present invention can further comprise a labeling agent. The labeling agent is the same as described above. The kit of the present invention may further comprise a secondary antibody capable of specifically recognizing an antibody against the analyte (a) and/or an antibody against the analyte (b) (primary antibody), or a carrier for solid-immobilizing an antibody (e.g., microtiter plate, glass beads and the like).

The present invention is hereinafter described in more detail by means of the following Examples, which, however, are given only for the sake of exemplification, and are not to be construed as limiting the scope of the invention.

EXAMPLE 1

Reference Example 1

Histopathological Examination and Peripheral Blood Lymphocyte Testing in Rats Receiving PLsis-inducing Compounds The following 10 kinds of commercially available drugs were examined as the test compounds for a potential of inducing PLsis by histopathological examination and peripheral blood lymphocyte testing. Amiodarone, imipramine, clomipramine, tamoxifen, chlorpromazine, quinacrine, chloroquine, amantadine and perhexiline were purchased from SIGMA Company; fluoxetine was purchased from Wako Pure Chemical Industries. Three kinds of drugs that cause angiitis/arteriopathy but have not been reported to cause lipidosis such as PLsis (roflumilast (WO 95/01338), Ariflo (WO 93/19749) and rolipram (Japanese Patent Examined Publication No. SHO-60-11028)) were used as negative controls.

475 male 5-week-old Crj: CD(SD)IGS rats (Charles River Japan Inc., produced in closed environment) (Sep. 3, 2002: 95 animals for Study Number 32-207/su, October 15: 95 animals for Study Number 32-231/su, November 5: 95 animals for Study Number 32-233/su, November 12: 95 animals for Study Number 32-234/su, November 28: 95 animals for Study Number 32-232/su) were obtained and acclimated for about 1 week. During that period, the animals were quarantined, examined for general conditions, and weighed. Animals showing no abnormalities were selected and randomly allocated to a total of 20 groups (88 animals in total) for individual studies, specifically to seven groups for urine collection each comprising four males, six groups (satellite groups) for determination of plasma drug concentrations each comprising three males, and seven groups undergoing premature autopsy each comprising six males. Their body weights at time of medication initiation at 6 weeks of age ranged from 171 to 200 g (Study Number 32-207/su: 172 to 198 g, Study Number 32-231/su: 171 to 198 g, Study Number 32-232/su: 176 to 200 g, Study Number 32-233/su: 178 to 199 g, Study Number 32-234/su: 172 to 197 g). The following experiments were performed using the prematurely autopsied animals.

The animals were individually housed in wire-net-based metal cages, and the individual cages were placed on a water-washable rack in a clean booth as randomized for the animal groups. Animal room environmental conditions comprised a room temperature of 20 to 26° C., a relative humidity of 40 to 70%, and a fresh air ventilation frequency of 8 to 25 times/hour, with a bright phase of 12 hours/day (lighting time: 7:00 am to 7:00 pm). The animals were fed a γ-ray-irradiated powder food (CR-LPF, Oriental Yeast Co., Ltd.) and had free access to the food along with tap water.

A dispersant/medium was added to each test material, and the mixture was stirred to prepare a high-dose suspension. The high-dose dosing suspension was diluted about 3 fold and 10 fold with dispersant/solvent to prepare intermediate- and low-dose dosing suspensions. The doses for the individual test materials were established as described below. [For $LD_{50}$, the Summary Basis of Approval (FDA) for each drug was referenced to.]

Amiodarone: 100, 300 and 1000 mg/kg/day ($LD_{50}$: not less than 3000 mg/kg)

Rationale: A high dose was established at a level permitting medication, and this was divided by a common ratio of about 3.

Imipramine: 100, 300 and 1000 mg/kg/day ($LD_{50}$: 1807 mg/kg)

Rationale: A high dose was established at a level about half $LD_{50}$, and this was divided by a common ratio of about 3.

Clomipramine: 100, 300 and 1000 mg/kg/day ($LD_{50}$: 914 mg/kg)

Rationale: A high dose was established at $LD_{50}$, and this was divided by a common ratio of about 3.

Tamoxifen: 100, 300 and 1000 mg/kg/day ($LD_{50}$: 1190 mg/kg)

Rationale: A high dose was established at $LD_{50}$, and this was divided by a common ratio of about 3.

Chlorpromazine: 10, 30 and 100 mg/kg/day ($LD_{50}$: 145 mg/kg)

Rationale: A high dose was established at a level about two-thirds of $LD_{50}$, and this was divided by a common ratio of about 3.

Quinacrine: 60, 200 and 600 mg/kg/day ($LD_{50}$: 900 mg/kg)

Rationale: A high dose was established at a level about two-thirds of $LD_{50}$, and this was divided by a common ratio of about 3.

chloroquine: 25, 75 and 250 mg/kg/day ($LD_{50}$: 330 mg/kg)

Rationale: A high dose was established at a level about two-thirds of $LD_{50}$, and this was divided by a common ratio of about 3.

Amantadine: 75, 250 and 750 mg/kg/day ($LD_{50}$: 1275 mg/kg)

Rationale: A high dose was established at a level about two-thirds of $LD_{50}$, and this was divided by a common ratio of about 3.

Perhexiline: 60, 200 and 600 mg/kg/day ($LD_{50}$: unknown)

Rationale: A high dose was established at a level at which a lesion is observed with 1 week administration, and this was divided by a common ratio of about 3.

Fluoxetine: 30, 100 and 300 mg/kg/day ($LD_{50}$: 452 mg/kg)

Rationale: A high dose was established at a level about two-thirds of $LD_{50}$, and this was divided by a common ratio of about 3.

Roflumilast: 1 and 3 mg/kg
Rationale: A high dose was established at a level at which angiitis/arteriopathy is observed, and one-third thereof was established as a low dose.
Ariflo: 30 and 100 mg/kg
Rationale: A high dose was established at a level at which angiitis/arteriopathy is observed, and one-third thereof was established as a low dose.
Rolipram: 30 and 100 mg/kg
Rationale: A high dose was established at a level at which angiitis/arteriopathy is observed, and one-third thereof was established as a low dose.
Control group: 0.5 w/v % methylcellulose solution
Each test drug was administered by gavage at a dosing liquid volume of 10 mL/kg/day once daily for 3 days (4 days for the negative control). The animals were examined for mortality, general conditions, body weight, food consumption and the like using PM4800 (Mettler) and EB3200D (Shimadzu Corporation).
After completion of the administration, livers, kidneys, hearts, spleens, lungs and mesenteric lymph nodes (livers, kidneys, hearts, spleens, lungs (including bronchi), stomachs (including short gastric arteries), mesenteries and testes for the negative control group) were sampled, with additional organs and tissues sampled for respective test materials, i.e., eyeballs for imipramine, brains and eyeballs for clomipramine, adrenal glands, pituitary glands and eyeballs for tamoxifen, brains and eyeballs for chlorpromazine, brains and femoral muscles for quinacrine, brains and eyeballs for chloroquine, brains and skins for perhexiline, and brains for fluoxetine (organs and tissues showing any change at autopsy for the negative control group); these sampled tissues were examined for histopathological changes by conventional methods of optical microscopy and electron microscopy.

Hematological examination was performed for parameters such as RBC count, hematocrit, hemoglobin concentration, mean corpuscular hemoglobin (MCH), mean corpuscular hemoglobin concentration (MCHC), mean corpuscular volume (MCV), platelet count, WBC count, reticulocyte count, differential WBC, and vacuolated lymphocyte ratio (for PLsis-inducing compounds only) using ADVIA120 (Bayer Medical Ltd.) and E-4000 (Sysmex Corporation).

The results for histopathological changes (electron microscopic findings of lipid accumulation) and vacuolated lymphocyte ratio in the PLsis-inducing compound administration group are shown in Table 1. For the 9 kinds of compounds except chlorpromazine, at least at the high dose, a remarkable increase in vacuolated lymphocyte ratio and histopathological changes in any target organ were observed. For chlorpromazine, it was found that PLsis positivity could not be determined by histopathological examination or vacuolated lymphocyte testing at any dose with the short-time administration for 3 days. In the negative control group, no histopathological findings suggesting lipidosis such as PLsis were obtained.

TABLE 1

| Compound | Dose (mg/kg/day) | Mean vacuolated lymphocyte ratio (%) | Histopathological changes (PLsis) | | | | |
|---|---|---|---|---|---|---|---|
| | | | Lung | Lymph node | Liver | Spleen | Others |
| Amantadine | 75 (death) | 1 | − | − | − | − | − |
| | 250 | 1 | − | − | − | − | − |
| | 750 | 61 | + | − | − | − | − |
| Amiodarone | 100 | 1 | − | − | − | − | − |
| | 300 | 33 | + | + | − | − | − |
| | 1000 | 40 | + | + | − | + | − |
| Chloroquine | 25 | 5 | − | − | − | − | − |
| | 75 | 24 | − | + | − | + | − |
| | 250 | 66 | − | + | − | + | − |
| Chlorpromazine | 100 | 2 | − | − | − | − | − |
| | 300 | 2 | − | − | − | − | − |
| | 1000 | 1 | − | − | − | − | − |
| Clomipramine | 100 (death) | 2 | − | − | − | − | − |
| | 300 | 30 | + | + | − | − | − |
| | 1000 | 38 | − | + | + | − | Kidney |
| Fluoxetine | 30 | 7 | + | + | + | − | Brain |
| | 100 | 28 | + | + | + | − | Brain |
| | 300 | 31 | + | − | + | − | − |
| Imipramine | 100 (death) | 20 | + | + | − | − | − |
| | 300 | 40 | + | + | − | − | − |
| | 1000 | ND | ND | ND | ND | ND | ND |
| Perhexiline | 60 | 2 | − | − | − | − | − |
| | 200 | 4 | + | + | − | − | − |
| | 600 | 52 | + | + | − | + | − |
| Quinacrine | 60 | 14 | + | − | + | − | − |
| | 200 | 32 | + | + | + | − | − |
| | 600 | 52 | + | + | + | − | − |
| Tamoxifen | 100 | 20 | + | + | − | − | − |
| | 300 | 39 | + | + | + | − | − |
| | 1000 | 40 | + | + | + | − | − |
| Roflumilast | 1 | ND | − | − | − | − | − |
| | 3 | ND | − | − | − | − | − |
| Ariflo | 30 | ND | − | − | − | − | − |
| | 100 | ND | − | − | − | − | − |

TABLE 1-continued

| Compound | Dose (mg/kg/day) | Mean vacuolated lymphocyte ratio (%) | Histopathological changes (PLsis) | | | | |
|---|---|---|---|---|---|---|---|
| | | | Lung | Lymph node | Liver | Spleen | Others |
| Rolipram | 30 | ND | − | − | − | − | − |
| | 100 | ND | − | − | − | − | − |

EXAMPLE 2

Changes in the Expression of Urinary PAG/Hippuric Acid Ratio by Administration of PLsis-inducing and Non-inducing Compounds Each test material was administered to rats for urine collection prepared in Example 1 (Reference Example 1) in the same manner; after 1 time and 3 times of administration, pooled urine was collected under fasting and water denial for about 6 hours. During the urine pooling, the collecting vessels were kept in an ice-cooled condition. After the urine collection, the urine was centrifuged at 1500×g for 10 minutes, and not less than 1 mL of the supernatant was collected and stored under freezing (below −70° C.) in a microtube in an ultralow-temperature freezer until the measurement. For the negative control group, 24-hour pooled urine was collected under ice cooling; after the urine collection, the urine was stored at −30° C. until the measurement.

$^1$H NMR was performed as described below. The reagents listed below were used without purification. Heavy water ($D_2O$) was purchased from ISOTEC. INC (USA); $NaH_2PO_4.2H_2O$ and $Na_2HPO_4.12H_2O$ were purchased from Kanto Chemical CO., Inc. (Tokyo). Sodium 3-(trimethylsilyl)-propionate-2,2,3,3,-$d_4$ (TSP) was purchased from ISOTEC INC (USA). NMR spectra were recorded using Unity INOVA600 (Varian) ($^1$H resonance frequency 599.59 MHz).

A phosphate buffer solution was prepared as described below. An about 0.2-mol/L $NaH_2PO_4$ solution and an about 0.2-mol/L $Na_2HPO_4$ solution were prepared using $NaH_2PO_4.2H_2O$ and $Na_2HPO_4.12H_2O$, respectively, after which the two solutions were mixed, and the mixture was adjusted to about pH 7.4 using a pH meter.

For internal standard solution, TSP was dissolved in heavy water to obtain a concentration of 11 mmol/L.

A 500-μL urine sample was collected in an Eppendorf tube, 250 μL of the above-described phosphate buffer solution was added, and the tube was allowed to stand at room temperature for about 10 minutes, after which the mixture was centrifuged at about 10° C. and 13000 rpm for about 10 minutes, and about 600 μL of the supernatant was collected and transferred to an NMR sample tube. Furthermore, about 60 μL of the TSP solution in heavy water was added to the NMR sample tube.

The nuclear magnetic resonance apparatus had a previously set probe enabling $^1$H nucleus measurement to enable $^1$H NMR measurement, and had been adjusted to a temperature of 25° C. The above-described NMR sample tube was set to the spectrometer and allowed to stand for about 10 minutes until the temperature stabilized, after which hardware settings, including resolution, tuning, 90° pulse measurement, observation center alignment to water signal and the like, as well as parameters were prepared. Operating conditions were set as shown below. Seqfil (pulse sequence): tnnoesy, sspul (steady state pulse): n (OFF), ss (steady state scans): 8 times, mix (mixing time): 100 ms, sw (sweep width): 8000 Hz, np (total number of points): 65536 points, d1 (relaxation delay): 4.904 sec, satpwr (saturation power): 10 dB, satdly (saturation time): 1 sec, number of scans: 64 times After measurement data was stored, Fourier transform was performed under the conditions shown below.

Number of points: 65536 points, window function: exponential window function lb=0.2 Hz Phase adjustment, reference to the methyl signal of TSP as 0 ppm and the like were performed.

After baseline correction using ACD/SpecManager (ACD Labs, Canada), the signal intensities of PAG (3.68 ppm), creatinine (4.06 ppm), and hippuric acid (7.83 ppm) were determined, and their ratio was calculated. The results are shown in Tables 2 and 3.

TABLE 2

| Compound | Dose (mg/kg/day) | PAG/ hippuric acid (%)[1] | PAG/ PAG + hippuric acid (%)[1] | PAG + hippuric acid/creatinine[1] | (PAG + hippuric acid) |
|---|---|---|---|---|---|
| Control (no administration) | 0 | 12.15 | 10.74 | 1.52 | (0.16 + 1.35) |
| Amantadine | 75 | 19.31 | 16.17 | 1.44 | (0.23 + 1.21) |
| | 250 | 19.69 | 16.18 | 1.21 | (0.20 + 1.02) |
| | 750 | 130.33 | 56.58 | 0.37 | (0.21 + 0.16) |
| Amiodarone | 100 | 16.12 | 13.68 | 1.69 | (0.23 + 1.47) |
| | 300 | 52.41* | 33.94* | 1.56 | (0.53 + 1.04) |
| | 1000 | 127.48* | 53.66* | 1.32 | (0.71 + 0.60) |
| Chloroquine | 25 | 15.42 | 13.25 | 1.34 | (0.18 + 1.16) |
| | 75 | 23.95* | 19.13* | 1.23 | (0.24 + 1.00) |
| | 250 | 69.41* | 40.08* | 1.29 | (0.52 + 0.76) |
| Chlorpromazine | 100 | 14.93 | 12.80 | 1.45 | (0.18 + 1.27) |
| | 300 | 14.51 | 12.57 | 1.63 | (0.21 + 1.42) |
| | 1000 | 104.13* | 42.20* | 0.86* | (0.30 + 0.56) |
| Clomipraxnine | 100 | 16.79 | 14.27 | 1.42 | (0.20 + 1.22) |
| | 300 | 62.72* | 33.36* | 0.74* | (0.20 + 0.52) |
| Fluoxetine | 30 | 18.58* | 15.60* | 1.13 | (0.17 + 0.96) |
| | 100 | 36.86* | 25.90* | 1.06 | (0.27 + 0.79) |
| | 300 | 56.32* | 31.88* | 0.67* | (0.20 + 0.47) |
| Imipramine | 100 | 39.63* | 28.23* | 1.21 | (0.34 + 0.87) |
| | 300 | 143.96* | 55.27* | 0.71* | (0.40 + 0.31) |
| Perhexiline | 60 | 11.39 | 10.16 | 1.47 | (0.15 + 1.31) |
| | 200 | 18.49 | 15.59* | 1.52 | (0.24 + 1.28) |
| | 600 | 146.97* | 45.67* | 0.75* | (0.31 + 0.44) |
| Quinacrine | 60 | 28.35* | 21.82* | 1.45 | (0.32 + 1.13) |
| | 200 | 91.89* | 46.42* | 1.58 | (0.75 + 0.83) |
| | 600 | 441.69* | 78.62* | 1.07* | (0.83 + 0.24) |
| Tamoxifen | 100 | 30.76* | 23.35* | 1.34 | (0.31 + 1.02) |
| | 300 | 120.23* | 54.01* | 1.16 | (0.63 + 0.53) |
| | 1000 | 143.34* | 54.00* | 1.58 | (0.91 + 0.67) |

[1]Mean (n = 3-4; n = 20 for control only)
*p < 0.025 (Williams test) vs control (non-administration group)
PAG: phenylacetylglycine

TABLE 3

| Compound | Dose (mg/kg/day) | PAG/ hippuric acid (%)[1] | PAG/ PAG + hippuric acid (%)[1] | PAG + hippuric acid/ creatinine[1] | (PAG + hippuric acid) |
|---|---|---|---|---|---|
| Control (no administration) | 0 | 11.95 | 9.92 | 1.31 | (0.13 + 1.18) |
| Roflumilast | 1 | 12.09 | 10.79 | 1.39 | (0.15 + 1.24) |
|  | 3 | 15.41 | 15.11 | 1.39 | (0.21 + 1.18) |
| Ariflo | 30 | 12.16 | 9.70 | 1.34 | (0.13 + 1.21) |
|  | 100 | 13.91 | 14.04 | 1.14 | (0.16 + 0.98) |
| Rolipram | 30 | 18.22 | 17.48 | 1.43 | (0.25 + 1.18) |
|  | 100 | 16.29 | 13.73 | 1.02 | (0.14 + 0.88) |

[1]Mean (n = 2-4)
PAG: phenylacetylglycine

For all PLsis-inducing compounds, the PAG/hippuric acid ratio and the PAG/(PAG+hippuric acid) ratio rose remarkably compared to the control group (Table 2). In the non-PLsis-inducing compound administration group, no significant difference was observed from control group even with high-dose administration (Table 3). When a correction is made based on creatinine content, the PAG content sometimes decreases with high-dose administration of a PLsis-inducing compound compared to intermediate-dose administration (see, for example, fluoxetine); it is found, however, that when the PAG/hippuric acid ratio or PAG/(PAG+hippuric acid) ratio is used as the index, high-dose administration produces higher values and more accurately reflects the extent of PLsis development. In the high-dose group, because food consumption decreases due to the aggravation of general conditions, and also because the Phe content entering the clearance pathways decreases, the accuracy of prediction is likely to fall when a change in PAG content is used as the only index, whereas the prediction is not influenced by the change in the amount of Phe taken when the PAG/hippuric acid ratio is used as the index; also, the accurate judgement is possible irrespective of the test animal's food consumption condition because the (PAG+hippuric acid) content reflects the amount of Phe taken when the PAG/(PAG+hippuric acid) ratio is used as the index.

When the PAG/hippuric acid ratio or PAG/(PAG+hippuric acid) ratio is used as the index, a remarkable increase is observed in the high-dose administration group for chlorpromazine as well; it was found that using this method, it is possible to quickly determine the presence or absence of the potential for inducing PLsis by 3-day administration.

EXAMPLE 3

Reference Example 2

Histopathological Examination and Peripheral Blood Lymphocyte Testing in Monkeys Receiving PLsis/Steatosis-inducing Compounds The following two kinds of commercially available drugs were examined as the test compounds for the potential for inducing PLsis/steatosis by histopathological examination and peripheral blood lymphocyte testing. Amiodarone and perhexiline were purchased from SIGMA Company.

Seven 3- to 5-year-old male cynomolgus monkeys (SICONBREC, Japan Wild Animal Inc., NAFOVANNY) were obtained and acclimated for about 1 week. During that period, the animals were quarantined, examined for general conditions, and weighed. Subsequently, the animals were allocated to four groups (5 animals in total) comprising 2 animals in the control group and 1 male in each treatment group, respectively.

The animals were individually housed in wire-net-based metal cages for monkeys, and the individual cages were placed on a water-washable rack as randomized for the animal groups. Animal room environmental conditions comprised a room temperature of 20 to 26° C., a relative humidity of 40 to 70%, and a fresh air ventilation frequency of 8 to 25 times/hour, with a bright phase of 12 hours/day (lighting time: 7:00 am to 7:00 pm). The animals were fed a γ-ray-irradiated solid food (Certified Primate Diet #5048, PMI Feeds Inc.) and had free access to the food along with tap water.

A dispersant/medium was added to each test material, and the mixture was stirred to prepare a high-dose suspension. The high-dose dosing suspension was diluted with the dispersant/solvent to prepare a low-dose dosing suspension. The doses for the individual test materials were established as described below.

Amiodarone: 60 and 300 mg/kg/day

Rationale: Established at levels about 10 times and 50 times the clinical dose for humans.

Perhexiline: 60 mg/kg/day

Rationale: Established at a level 10 times the clinical dose for humans.

Control group: 0.5 w/v % methylcellulose solution

Dosing suspension volume: Administered by gavage at 5 mL/kg/day once daily for 7 days.

After completion of the administration, livers, kidneys, hearts, spleens, lungs, mesenteric lymph nodes, eyeballs, testes and brains were collected from all animals, and examined for histopathological changes by conventional method of optical microscopy. Additionally, blood samples were collected in the pre-dosing period, on the first day of administration, and on days 2 and 6 of treatment period, blood smear specimens were prepared, and vacuolated lymphocyte ratios were determined.

The results for histopathological changes and vacuolated lymphocytes ratios in the PLsis/steatosis-inducing compound treatment groups are shown in Table 4. In the amiodarone 300 mg/kg and perhexiline 60 mg/kg groups, an increase in vacuolated lymphocyte ratio and histopathological changes in any target organ were observed. In the amiodarone 60 mg/kg group, induction of PLsis/steatosis was not observed. In the control group, no histopathological findings suggesting lipidosis such as PLsis/steatosis were obtained.

TABLE 4

| | Male cynomolgus monkeys, 3 to 5 years of age at time of medication initiation | | | |
|---|---|---|---|---|
| Test material | Solvent[a] | Amiodarone | | Perhexilin |
| Dose (mg/kg/day) | 0 | 60 | 300 | 60 |
| Dosing suspension volume (mL/kg/day) | 5 | 5 | 5 | 5 |
| Number of animals (M) | 2 | 1 | 1 | 1 |
| Urinary PAGN/ hippuric acid ratio | Pre | 1.31 | 1.05 | 1.22 | 1.10 |
| | Day 0 | 1.55 | 1.87 | 1.11 | 2.17 |
| | Day 2 | 2.14 | 1.79 | 3.04 | 1.43 |
| | Day 6 | 2.48 | 3.87 | ↑17.62 | ↑12.89 |
| Vacuolated lymphocyte ratio (%) | Pre | 0 | 1 | 2 | 1 |
| | Day 0 | 3 | 0 | 3 | 7 |
| | Day 2 | 0 | 3 | ↑19 | 9 |
| | Day 6 | 4 | 6 | ↑13 | ↑22 |

TABLE 4-continued

| | Male cynomolgus monkeys, 3 to 5 years of age at time of medication initiation | | |
|---|---|---|---|
| Test material | Solvent[a)] | Amiodarone | Perhexilin |
| Histopathological examination | — — | — — | Lungs: foamy cell infiltration Liver: vacuolation of hepatocyte Kidney: vacuolation of renal tubule | Lungs: foamy cell infiltration Liver: vacuolation of hepatocyte |

—: no abnormalities,
↑: increased value,
↓: decreased value,
PAGN: phenylacetylglutamine
[a)]0.5 w/v % methylcellulose solution

EXAMPLE 4

Changes in Urinary PAGN/Hippuric Acid Ratio by Induction of PLsis/Steatosis

Pooled urine was collected from the monkeys in the Example above under fasting for about 6 hours in the pre-dosing period (Pre), on the first day of administration (Day 0), and on days 2 and 6 of treatment period (Days 2 and 6). After the urine collection, the urine was centrifuged at 1500×g for 10 minutes, and not less than 1 mL of the supernatant was transferred to a microtube, after which it was stored under freezing (below −70° C.) in an ultralow-temperature freezer until measurement.

$^1$H NMR was performed as described below. Reagents were used without purification. Heavy water ($D_2O$) was purchased from ISOTEC. INC(USA); $NaH_2PO_4.2H_2O$ and $Na_2HPO_4.12H_2O$ were purchased from Kanto Chemical CO., Inc. (Tokyo). Sodium 3-(trimethylsilyl)-propionate-2,2,3,3,-$d_4$ (TSP) was purchased from ISOTEC. INC (USA). NMR spectra were determined using Unity INOVA600 (Varian) ($^1$H resonance frequency 599.59 MHz).

A phosphate buffer solution was prepared as described below. An about 0.2-mol/L $NaH_2PO_4$ solution and an about 0.2-mol/L $Na_2HPO_4$ solution were prepared using $NaH_2PO_4.2H_2O$ and $Na_2HPO_4.12H_2O$, respectively, after which the two solutions were mixed, and the mixture was adjusted to about pH 7.4 using a pH meter.

For internal standard solution, TSP was dissolved in heavy water to obtain a concentration of 11 mmol/L.

A 500-µL urine sample was collected in an Eppendorf tube, 250 µL of the above-described phosphate buffer solution was added, and the tube was allowed to stand at room temperature for about 10 minutes, after which the mixture was centrifuged at about 10° C. and 13000 rpm for about 10 minutes, and about 600 µL of the supernatant was collected and transferred to an NMR sample tube. Furthermore, about 60 µL of the TSP solution in heavy water was added to the NMR sample tube.

The nuclear magnetic resonance apparatus had a previously set probe enabling $^1$H nucleus measurement to enable $^1$H NMR measurement, and was adjusted to a temperature of 25° C. The above-described NMR sample tube was set to the spectrometer and allowed to stand for about 10 minutes until the temperature stabilized, after which hardware settings, including resolution, tuning, 90° pulse measurement, observation center alignment to water signal and the like, as well as parameters were prepared. Operating conditions were set as shown below.

Seqfil (pulse sequence): tnnoesy, sspul (steady state pulse): n (OFF), ss (steady state scans): 8 times, mix (mixing time): 100 ms, sw (sweep width): 8000 Hz, np (total number of points): 65536 points, d1 (relaxation delay): 4.904 sec, satpwr (saturation power): 10 dB, satdly (saturation time): 1 sec, number of scans: 64 times After the measurement data was stored, Fourier transform was performed under the conditions shown below. Number of points: 65536 points, window function: exponential window function lb=0.2 Hz Phase adjustment, reference to the methyl signal of TSP as 0 ppm and the like were performed.

After baseline correction using ACD/SpecManager (ACD Labs, Canada), the ratio of the two substances (PAGN/hippuric acid ratio) was calculated from the integral values of the signals at 7.42 ppm (t, 8.0 Hz) for PAGN and 7.55 ppm (t, 8.0 Hz) for hippuric acid. The results are shown in Table 4.

In the animals having PLsis/steatosis induced (animals receiving 300 mg/kg of amiodarone or 60 mg/kg of perhexiline), the PAGN/hippuric acid ratio increased compared to the control group (Table 4). Meantime, in the animals not having PLsis/steatosis induced (animals receiving 60 mg/kg amiodarone), no significant difference was observed in PAGN/hippuric acid ratio compared to the control group (Table 4).

In the animals having PLsis/steatosis induced, the total excretion of hippuric acid and PAGN decreased compared to the control group. This was attributed to a decrease in the content of excess Phe not available for Tyr synthesis because of remarkably decreased food consumption with drug administration compared to the control group. However, because the hippuric acid content reduction rate was much greater than the PAGN content reduction rate, PLsis/steatosis-inducing compounds could be accurately identified when the PAGN/hippuric acid ratio was used as the index. This result can be said to demonstrate the superiority of the present invention to the conventional prediction method for PLsis/steatosis, which employs an increase in PAG or PAGN as the only index.

EXAMPLE 5

(1) Preparation of Anti-PAGN Antibody and Anti-hippuric Acid Antibody

PAGN is prepared according to the method described in Example 1 of the description for U.S. Pat. No. 5,100,807.

Hippuric acid is purchased from SIGMA Company. A PAGN-bovine serum albumin (BSA) conjugate and a hippuric acid-BSA conjugate are prepared in accordance with the method described in Example 2 of the description for the same patent. After each conjugate obtained is admixed with an equal volume of Freund's complete adjuvant (FCA), the mixture is intradermally administered to female rabbits (Japanese White breed, body weight 2.7 to 2.8 kg). Boosters are performed at 3-week intervals; 1 week after the final booster, whole blood is collected from carotid artery under Nembutal anesthesia and incubated at room temperature for 2.5 hours, after which the blood is centrifuged at 2000×g (4000 rpm) for 10 minutes to obtain an antiserum. After the serum is dissolved by adding sodium sulfate little by little, the solution is centrifuged, and the precipitate is recovered and dissolved in phosphate buffer solution (pH 6.3), after which the solution is dialyzed against the same buffer solution at 4°

C. for 5 hours, after which the external dialytic liquid is replaced with a fresh supply, and this is followed by further dialysis overnight. The supernatant is subjected to chromatography through a DE52-cellulose column equilibrated with the same buffer solution to obtain an IgG fraction. After each IgG is solid-immobilized, PAGN or hippuric acid and HRP-labeled PAGN (hippuric acid) prepared by a conventional method are competitively reacted, peroxidase activity is measured, and it is confirmed that both antibodies do not cross-react with each other.

(2) Detection of PAGN and Hippuric Acid

BSA-containing PBS solutions of the rabbit anti-PAGN IgG and rabbit anti-hippuric acid IgG obtained in (1) above, the urine sample collected in Example 4, and fluorescein-labeled PAGN and pyrene-labeled hippuric acid prepared by a conventional method are added to a tube and reacted for 60 minutes, after which fluorescein fluorescence is measured at an excitation wavelength of 490 nm and a fluorescence wavelength of 520 nm, and pyrene fluorescence is measured at an excitation wavelength of 350 nm and a fluorescence wavelength of 390 nm, using Full-Range BEACON® 2000. From a working curve previously generated using standard solutions of PAGN and hippuric acid, PAGN and hippuric acid contents in the urine sample are calculated, respectively.

EXAMPLE 6

Measurement of Urinary Hippuric Acid and PAG Concentrations by LC-MS/MS with Administration of PLsis-inducing Compounds With amiodarone, imipramine, tamoxifen and quinacrine, which produced histopathological changes in Example 1, as the test compounds, rat urinary hippuric acid and PAG concentrations were measured by a quantitative method using a high performance liquid chromatograph/triple quadrupole mass spectrometer (LC-MS/MS).

One hundred 5-week-old male Crj: CD(SD)IGS rats (Charles River Japan Inc., produced in closed environment) (Nov. 16, 2004; Study Number 34-351/su) were obtained and acclimated for about 1 week. During that period, the animals were quarantined, examined for general conditions, and weighed. Animals showing no abnormalities were selected and randomly allocated to five groups for urine collection each comprising four males.

The animals were individually housed in wire-net-based metal cages, and the individual cages were placed on water-washable rack in a clean booth as randomized for the animal groups. Animal room environmental conditions comprised a room temperature of 20 to 26° C., a relative humidity of 40 to 70%, and a fresh air ventilation frequency of 8 to 25 times/hour, with a bright phase of 12 hours/day (lighting time: 7:00 am to 7:00 pm). The animals were fed a γ-ray-irradiated powder food (CR-LPF, Oriental Yeast Co., Ltd.) and had free access to the food along with tap water.

A dispersant/medium was added to each test material, and the mixture was stirred to prepare dosing suspensions. The doses of the individual test materials were established as described below.

Amiodarone: 300 mg/kg/day
Imipramine: 100 mg/kg/day
Tamoxifen: 100 mg/kg/day
Quinacrine: 60 mg/kg/day
Control group: 0.5 w/v % methylcellulose solution Each test material was administered by gavage at a dosing suspension volume of 10 mL/kg/day once daily for 7 days.

After completion of the administration, pooled urine was collected with ice cooling from all animals under fasting and water denial for about 6 hours.

After the urine collection, the urine was centrifuged at 1500×g for 10 minutes, and not less than 1 mL of the supernatant was collected and stored in a microtube under freezing (below −15° C.) in a low-temperature freezer until the measurement.

Quantitative analyses of rat urinary hippuric acid and PAG by LC-MS/MS were performed as described below. As the standard substances, hippuric acid (Lot No. PKE1876, content 99.8%) and PAG (Lot No. PKG7583, content 99.4%) were obtained from Wako Pure Chemical, hippuric acid-d5 (Lot No. H63P3, d5 conversion rate 99.3%) was obtained from CDN Isotopes, and PAG-d4 (Lot No. B18607-060-17, d4 conversion rate 100.0%) was synthesized in-house. Acetonitrile, ammonium formate, formic acid, ammonium acetate and methanol were all obtained from Wako Pure Chemical.

The HPLC system used was the LC-10ADvp system (Shimadzu Corporation); the MS/MS system used was API3000 (AB/MDS SCIEX).

20 µL of 50% acetonitrile, 10 µL of a 50% acetonitrile solution of hippuric acid-d5 and PAG-d5 (internal standard solution, I.S.) and 1 mL of 50% acetonitrile were added to a 20-µL urine sample or QC sample, and the mixture was stirred for 5 seconds, after which the resulting solution was centrifuged at room temperature and 13000 rpm for 5 minutes. 20 µL of the centrifugation supernatant was collected, 1 mL of HPLC mobile phase ((A):(B)=95:5, v/v) was added, and the mixture was stirred for 10 seconds; the resulting sample solution was subjected to LC/MS/MS analysis.

20 µL of hippuric acid or PAG-diluted standard and 10 µL of internal standard solution were added to 20 µL of a 10 mmol/L aqueous solution of ammonium acetate, the mixture was treated in the same manner, and this sample was used as the sample for standard working curve. Samples for standard working curves for hippuric acid and PAG were prepared to obtain the final concentration shown below. Hippuric acid: 5000, 4000, 2000, 1000, 500, 200, 100 and 50 µg/mL, PAG concentrations: 1000, 500, 400, 200, 100, 50, 20, 10 and 5 µg/mL.

QC samples were prepared by measuring the concentrations of hippuric acid and PAG, which are endogenous ingredients of the rat control urine, using the standard working curves, and adding hippuric acid and PAG-diluted standard solutions to these samples to prepare QC-H and QC-M. QC-H was diluted 20 fold with the 10 mmol/L aqueous solution of ammonium acetate to prepare QC-L.

Chromatographic separation by HPLC was performed in the gradient mode using L-Column ODS (particle diameter; 5 µm, inside diameter; 2.1 mm, length; 50 mm, Chemicals Evaluation and Research Institute, Japan) as the separation column. 10 mmol/L ammonium formate/formic acid (500:1, v/v) as mobile phase (A) and acetonitrile/formic acid (500:1, v/v) as mobile phase (B) were supplied at a flow rate of 0.2 mL/min. The gradient program comprised linearly increasing the mobile phase (B) concentration from 5% at 0 minutes (at start of analysis) to 60% at 3 minutes, then to 80% by 3.2 minutes.

Subsequently, the mobile phase (B) was supplied at 80% until 5 minutes, the concentration was reduced to 5% after 5.1 minutes, and the mobile phase (B) was supplied under the same conditions until completion of the analysis (10 minutes). The eluate obtained at an analytical time of 3.0-4.5 minutes was introduced to the MS/MS using a switching valve. The analysis was performed at a column temperature of 40° C. and a sample injection volume of 10 µL.

MS/MS analysis was performed in the ionization mode using a turbo ion spray, and ions were detected by selected reaction monitoring (SRM) in the cation mode. The ion spray was performed using zero air at a voltage of 4.2 kV. Nitrogen was used for the collision induction decomposition of ions. As monitor ions, precursor ions and fragment ions were set at hippuric acid; 180 Da→105 Da, PAG; 194 Da→91 Da, hippuric acid d-5; 185 Da→110 Da, PAG-d4; 198 Da→93 Da, respectively.

Using the peak area ratios of hippuric acid and PAG to the respective I.S., the hippuric acid and PAG concentrations in each sample were calculated from the regression equation (weighting of 1/concentration) of the standard working curve. The results are shown in Table 5.

TABLE 5

| Compound | Hippuric acid[1),2)] | PAG[1),2)] | PAG/hippuric acid ratio[1)] |
| --- | --- | --- | --- |
| Control | 1401.3 ± 729.4 | 92.5 ± 46.6 | 0.0709 ± 0.0334 |
| Amiodarone | 894.9 ± 144.2 | 765.9 ± 301.6 | 0.8850 ± 0.4434 |
| Imipramine | 888.9 ± 249.2 | 291.9 ± 75.7 | 0.3385 ± 0.0977 |
| Tamoxifen | 800.3 ± 483.2 | 292.6 ± 178.1 | 0.5169 ± 0.5311 |
| Quinacrine | 869.3 ± 240.8 | 188.0 ± 78.1 | 0.2178 ± 0.0919 |

[1)]Mean ± SD (n = 4)
[2)]Unit of measurement: μg/mL

The PAG/hippuric acid concentration ratios in the amiodarone, imipramine, tamoxifen, and quinacrine administration groups increased compared to the control group (Table 5). Additionally, increases and decreases in the urinary concentrations of hippuric acid and PAG could be accurately evaluated. This analytical method was found to enable quick determination of the presence or absence of the potential for inducing PLsis in the prediction method for Plsis/steatosis because an analysis in a short time of 10 minutes per analytical run is possible, and also because absolute concentrations of hippuric acid and PAG in urine can be evaluated.

INDUSTRIAL APPLICABILITY

Because the prediction method of the present invention is useful as a screening tool for quickly identifying toxic compounds in the initial stage of development, and streamlining the selection of lead compound because it enables the prediction of drug-induced lipidosis at high accuracy and high sensitivity, and also the determination of positivity with short-time administration even for a compound with which no histopathological changes are manifested unless the compound is administered for a long time.

Furthermore, the prediction/diagnostic method of the present invention is highly useful in the clinical diagnosis of lipidosis and diseases related thereto because it enables non-invasive diagnoses provided that a peripheral humoral fluid such as urine or plasma is the sample.

This application is based on patent application Nos. 2003-434151 (filing date: Dec. 26, 2003) and 2004-168849 (filing date: Jun. 7, 2004) filed in Japan, the contents of which are incorporated in full herein by this reference.

The invention claimed is:

1. A prediction method for lipidosis caused by a compound, which comprises:
    (1) detecting (a) phenylacetylglycine and/or phenylacetylglutamine, or an optionally chosen metabolic intermediate in the metabolic pathway from phenylalanine to phenylacetylglycine or phenylacetylglutamine, and (b) hippuric acid or an optionally chosen metabolic intermediate in the metabolic pathway from phenylalanine to hippuric acid, in a sample collected from a mammal receiving the compound or a mammalian cell or tissue culture exposed to the compound; and
    (2) predicting the compound's potential for inducing lipidosis with the quantitative ratio of (a):(b), (a):[(a)+(b)] or (b):[(a)+(b)] as an index, wherein when the quantitative ratio differs from the same quantitative ratio obtained in a sample collected from a mammal not receiving the compound or obtained from a mammalian cell or tissue culture not exposed to the compound, the compound is predicted to induce lipidosis.

2. The method of claim 1, wherein the quantitative ratio of phenylacetylglycine and/or phenylacetylglutamine and hippuric acid is used as the index.

3. The method of claim 1, wherein the sample is urine, serum or plasma.

4. The method of claim 1, wherein the cell or tissue is derived from the liver, kidney or lung, or is a lymphocyte.

5. The method of claim 1, wherein the lipidosis develops as one or more conditions selected from the group consisting of phospholipidosis, steatosis and sphingolipidosis.

6. A diagnostic method for the diagnosis of lipidosis or a disease related thereto in a mammal, which comprises:
    (1) detecting (a) phenylacetylglycine and/or phenylacetylglutamine, or an optionally chosen metabolic intermediate in the metabolic pathway from phenylalanine to phenylacetylglycine or phenylacetylglutamine, and (b) hippuric acid or an optionally chosen metabolic intermediate in the metabolic pathway from phenylalanine to hippuric acid, in a sample collected from a mammal, and
    (2) making a diagnosis with the quantitative ratio of (a):(b), (a):[(a)+(b)] or (b):[(a)+(b)] as an index, wherein when the quantitative ratio differs from the same quantitative ratio obtained in a sample collected from a normal mammal, a diagnosis of lipidosis or a disease related thereto is made.

7. The method of claim 6, wherein the quantitative ratio of phenylacetylglycine and/or phenylacetylglutamine and hippuric acid is used the index.

8. The method of claim 6, wherein the sample is urine, serum or plasma.

9. The method of claim 6, wherein the lipidosis is hereditary lipidosis, drug-induced lipidosis or fatty acid metabolism homeostasis abnormalities.

10. The method of claim 6, wherein the disease is selected from the group consisting of hyperlipemia, atherosclerosis, arteriosclerosis, myocardial infarction, fatty liver, hepatitis, liver cirrhosis, diabetes mellitus, dementia, Alzheimer's disease, heart disease and chronic fatigue syndrome.

* * * * *